United States Patent
Lee et al.

(10) Patent No.: US 12,420,103 B1
(45) Date of Patent: Sep. 23, 2025

(54) NEUROSTIMULATION LEADS WITH REDUCED CURRENT LEAKAGE

(71) Applicant: Axonics, Inc., Irvine, CA (US)

(72) Inventors: Henry Lee, Irvine, CA (US); Prabodh Mathur, Laguna Niguel, CA (US); Guangqiang Jiang, Irvine, CA (US)

(73) Assignee: Axonics, Inc., Irvine, CA (US)

( * ) Notice: Subject to any disclaimer, the term of this patent is extended or adjusted under 35 U.S.C. 154(b) by 210 days.

(21) Appl. No.: 17/405,721

(22) Filed: Aug. 18, 2021

Related U.S. Application Data

(60) Provisional application No. 63/068,299, filed on Aug. 20, 2020.

(51) Int. Cl.
| | |
|---|---|
| *A61N 1/375* | (2006.01) |
| *A61N 1/05* | (2006.01) |
| *A61N 1/36* | (2006.01) |
| *B29C 45/26* | (2006.01) |
| *B29K 75/00* | (2006.01) |

(52) U.S. Cl.
CPC .............. *A61N 1/3752* (2013.01); *A61N 1/05* (2013.01); *A61N 1/36142* (2013.01); *B29C 45/261* (2013.01); *B29K 2075/00* (2013.01)

(58) Field of Classification Search
CPC .... A61N 1/3752; A61N 1/05; A61N 1/36142; B29C 45/261; B29K 2075/00
See application file for complete search history.

(56) References Cited

U.S. PATENT DOCUMENTS

| | | | |
|---|---|---|---|
| 3,057,356 | A | 10/1962 | Greatbatch |
| 3,348,548 | A | 10/1967 | Chardack |
| 3,646,940 | A | 3/1972 | Timm et al. |
| 3,824,129 | A | 7/1974 | Fagan, Jr. |
| 3,825,015 | A | 7/1974 | Berkovits |

(Continued)

FOREIGN PATENT DOCUMENTS

| | | |
|---|---|---|
| AT | 520440 | 9/2011 |
| AU | 4664800 | 11/2000 |

(Continued)

OTHER PUBLICATIONS

US 9,601,939 B2, 03/2017, Cong et al. (withdrawn)

(Continued)

*Primary Examiner* — Mark W. Bockelman
(74) *Attorney, Agent, or Firm* — Seager Tufte & Wickhem, LLP

(57) ABSTRACT

Embodiments include implantable neurostimulation leads configured to reduce current leakage following implantation in a patient's body, and methods of manufacturing such leads. A lead includes a lead body with proximal apertures and distal apertures; a lumen extending through the lead body; electrodes at a distal portion of the lead body and connector interfaces at a proximal portion of the lead body; conductors extending through the lead body, with their proximal ends exiting via respective proximal apertures to couple with a respective connector interfaces, and their distal ends exiting the interior of the lead body via respective distal apertures to couple with a respective electrodes; and an electrically nonconductive filler element for occupying gaps in the interior of the lead body resulting from the exit of conductors from the lead body.

23 Claims, 7 Drawing Sheets

(56) References Cited

U.S. PATENT DOCUMENTS

| | | |
|---|---|---|
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,135,518 A | 1/1979 | Dutcher |
| 4,141,365 A | 2/1979 | Fischell et al. |
| 4,166,469 A | 9/1979 | Littleford |
| 4,236,529 A | 12/1980 | Little |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | deCoriolis et al. |
| 5,366,493 A | 11/1994 | Scheiner et al. |
| 5,439,485 A | 8/1995 | Mar et al. |
| 5,476,499 A | 12/1995 | Hirschberg |
| 5,484,445 A | 1/1996 | Knuth |
| 5,545,206 A | 8/1996 | Carson |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,683,447 A | 11/1997 | Bush et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,191,365 B1 | 2/2001 | Avellanet |
| 6,208,894 B1 | 3/2001 | Schulman et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,240,322 B1 | 5/2001 | Peterfeso et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,315,721 B2 | 11/2001 | Schulman et al. |
| 6,316,909 B1 | 11/2001 | Honda et al. |
| 6,321,118 B1 | 11/2001 | Hahn |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,477,427 B1 * | 11/2002 | Stolz ............... A61N 1/05 607/116 |
| 6,500,141 B1 | 12/2002 | Irion et al. |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,542,846 B1 | 4/2003 | Miller et al. |
| 6,553,263 B1 | 4/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |
| 6,664,763 B2 | 12/2003 | Echarri et al. |
| 6,685,638 B1 | 2/2004 | Taylor et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,757,970 B1 * | 7/2004 | Kuzma ............... A61N 1/0551 600/374 |
| 6,792,314 B2 | 9/2004 | Byers et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,092,764 B2 | 8/2006 | Williams et al. |
| 7,127,298 B1 | 10/2006 | He et al. |

(56) References Cited

U.S. PATENT DOCUMENTS

| | | |
|---|---|---|
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,590,451 B2 | 9/2009 | Tronnes et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,676,275 B1 | 3/2010 | Farazi et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,881,783 B2 | 2/2011 | Bonde et al. |
| 7,894,913 B2 | 2/2011 | Boggs et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,443 B2 | 9/2011 | Schleicher et al. |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,271,098 B2 | 9/2012 | Swanson et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,364,281 B2 | 1/2013 | Duncan et al. |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |

(56) References Cited

U.S. PATENT DOCUMENTS

| | | |
|---|---|---|
| 8,706,229 B2 | 4/2014 | Lahti et al. |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,855,767 B2 | 10/2014 | Faltys et al. |
| 8,918,174 B2 | 12/2014 | Woods et al. |
| 8,954,148 B2 | 2/2015 | Labbe et al. |
| 8,989,861 B2 | 3/2015 | Su et al. |
| 9,002,476 B2 | 4/2015 | Geroy et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,117,680 B2 | 8/2015 | Fisk |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,427,574 B2 | 8/2016 | Lee et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,802,038 B2 | 10/2017 | Lee et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,844,661 B2 | 12/2017 | Franz et al. |
| 9,849,278 B2 | 12/2017 | Spinelli et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |

(56) References Cited

U.S. PATENT DOCUMENTS

| | | |
|---|---|---|
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | LeBaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,478,619 B2 | 11/2019 | Lee et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0140399 A1 | 10/2002 | Echarri et al. |
| 2002/0156513 A1 | 10/2002 | Borkan |
| 2002/0177884 A1 | 11/2002 | Ahn et al. |
| 2003/0023296 A1 | 1/2003 | Osypka |
| 2003/0028231 A1 | 2/2003 | Partridge et al. |
| 2003/0114899 A1 | 6/2003 | Woods et al. |
| 2003/0212440 A1 | 11/2003 | Boveja |
| 2003/0236562 A1* | 12/2003 | Kuzma ............... B29C 33/126 607/122 |
| 2004/0087984 A1 | 5/2004 | Kupecki et al. |
| 2004/0098068 A1 | 5/2004 | Carbunaru et al. |
| 2004/0172115 A1 | 9/2004 | Miazga et al. |
| 2004/0210290 A1 | 10/2004 | Omar-Pasha |
| 2004/0230282 A1 | 11/2004 | Cates et al. |
| 2004/0250820 A1 | 12/2004 | Forsell |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0104577 A1 | 5/2005 | Matei et al. |
| 2005/0187590 A1 | 8/2005 | Boveja et al. |
| 2006/0041295 A1 | 2/2006 | Osypka |
| 2006/0074412 A1 | 4/2006 | Zerfas et al. |
| 2006/0095078 A1 | 5/2006 | Tronnes |
| 2006/0122676 A1 | 6/2006 | Ko et al. |
| 2006/0142822 A1 | 6/2006 | Tulgar |
| 2006/0149345 A1 | 7/2006 | Boggs, II et al. |
| 2006/0200205 A1 | 9/2006 | Haller |
| 2006/0206166 A1 | 9/2006 | Weiner |
| 2007/0027517 A1 | 2/2007 | Bischoff et al. |
| 2007/0032836 A1 | 2/2007 | Thrope et al. |
| 2007/0073295 A1 | 3/2007 | Biedermann et al. |
| 2007/0168004 A1* | 7/2007 | Walter ............... A61N 1/0551 607/116 |
| 2007/0239224 A1 | 10/2007 | Bennett et al. |
| 2007/0255368 A1 | 11/2007 | Bonde et al. |
| 2007/0255369 A1 | 11/2007 | Bonde et al. |
| 2007/0265675 A1 | 11/2007 | Lund et al. |
| 2007/0293914 A1 | 12/2007 | Woods et al. |
| 2008/0065182 A1 | 3/2008 | Strother et al. |
| 2008/0103570 A1 | 5/2008 | Gerber |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0183236 A1 | 7/2008 | Gerber |
| 2008/0183257 A1 | 7/2008 | Imran et al. |
| 2009/0012592 A1 | 1/2009 | Buysman et al. |
| 2010/0076254 A1 | 3/2010 | Jimenez et al. |
| 2010/0076534 A1 | 3/2010 | Mock |
| 2010/0100158 A1 | 4/2010 | Thrope et al. |
| 2010/0121421 A1 | 5/2010 | Duncan et al. |
| 2010/0160997 A1 | 6/2010 | Johnson et al. |
| 2010/0256696 A1 | 10/2010 | Schleicher et al. |
| 2011/0251662 A1 | 10/2011 | Griswold et al. |
| 2011/0257500 A1 | 10/2011 | Wells et al. |
| 2011/0257701 A1 | 10/2011 | Strother et al. |
| 2011/0270269 A1 | 11/2011 | Swoyer et al. |
| 2011/0282416 A1 | 11/2011 | Hamann et al. |
| 2011/0301663 A1 | 12/2011 | Wang et al. |
| 2011/0301667 A1 | 12/2011 | Olson et al. |
| 2011/0313427 A1 | 12/2011 | Gindele et al. |
| 2012/0041512 A1 | 2/2012 | Weiner |
| 2012/0046712 A1 | 2/2012 | Woods et al. |
| 2012/0053665 A1 | 3/2012 | Stolz et al. |
| 2012/0095478 A1 | 4/2012 | Wang et al. |
| 2012/0130448 A1 | 5/2012 | Woods et al. |
| 2012/0179221 A1 | 7/2012 | Reddy et al. |
| 2012/0191169 A1 | 7/2012 | Rothstein et al. |
| 2012/0203320 A1 | 8/2012 | DiGiore et al. |
| 2012/0276854 A1 | 11/2012 | Joshi et al. |
| 2012/0276856 A1 | 11/2012 | Joshi et al. |
| 2012/0310317 A1 | 12/2012 | Lund et al. |
| 2012/0330354 A1 | 12/2012 | Kane et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0018445 A1 | 1/2013 | Sakai et al. |
| 2013/0018447 A1 | 1/2013 | Ollivier et al. |
| 2013/0023724 A1 | 1/2013 | Allen et al. |
| 2013/0131766 A1 | 5/2013 | Crosby et al. |
| 2013/0150925 A1 | 6/2013 | Vamos et al. |
| 2013/0150936 A1 | 6/2013 | Takahashi |
| 2013/0150939 A1 | 6/2013 | Burnes et al. |
| 2013/0184773 A1 | 7/2013 | Libbus et al. |
| 2013/0197608 A1 | 8/2013 | Eiger |
| 2013/0207863 A1 | 8/2013 | Joshi |
| 2013/0310894 A1 | 11/2013 | Trier |
| 2013/0331909 A1 | 12/2013 | Gerber |
| 2014/0031661 A1 | 1/2014 | Clark et al. |
| 2014/0081363 A1 | 3/2014 | Clark et al. |
| 2014/0128952 A1 | 5/2014 | Jang et al. |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0088227 A1 | 3/2015 | Shishilla et al. |
| 2015/0214604 A1 | 7/2015 | Zhao et al. |
| 2016/0045724 A1 | 2/2016 | Lee et al. |
| 2017/0197079 A1 | 7/2017 | Illegems et al. |
| 2017/0340878 A1 | 11/2017 | Wahlstrand et al. |
| 2018/0021587 A1 | 1/2018 | Strother et al. |
| 2018/0036477 A1 | 2/2018 | Olson et al. |
| 2019/0269918 A1 | 9/2019 | Parker |

(56) References Cited

U.S. PATENT DOCUMENTS

| | | | |
|---|---|---|---|
| 2019/0314635 | A1* | 10/2019 | Iyer ................. A61N 1/3754 |
| 2019/0351244 | A1 | 11/2019 | Shishilla et al. |
| 2019/0358395 | A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CA | 2957962 | 5/2018 |
| CN | 101678203 | 3/2010 |
| CN | 102065947 | 5/2011 |
| CN | 103702713 | 4/2014 |
| DE | 3146182 | 6/1983 |
| EP | 656218 | 6/1995 |
| EP | 1205004 | 5/2002 |
| EP | 1680182 | 7/2006 |
| EP | 2243509 | 10/2010 |
| ES | 2395128 | 2/2013 |
| HK | 1098715 | 3/2012 |
| JP | 6510209 | 11/1994 |
| JP | 2007268293 | 10/2007 |
| JP | 4125357 | 7/2008 |
| WO | 9820933 | 5/1998 |
| WO | 9918879 | 4/1999 |
| WO | 9934870 | 7/1999 |
| WO | 9942173 | 8/1999 |
| WO | 27469 | 5/2000 |
| WO | 56677 | 9/2000 |
| WO | 65682 | 11/2000 |
| WO | 69012 | 11/2000 |
| WO | 183029 | 11/2001 |
| WO | 209808 | 2/2002 |
| WO | 3084433 | 10/2003 |
| WO | 2004021876 | 3/2004 |
| WO | 2004103465 | 12/2004 |
| WO | 2005079295 | 9/2005 |
| WO | 2005081740 | 9/2005 |
| WO | 2006116205 | 11/2006 |
| WO | 2007022180 | 2/2007 |
| WO | 2008021524 | 2/2008 |
| WO | 2008094952 | 8/2008 |
| WO | 2008153726 | 12/2008 |
| WO | 2009102536 | 8/2009 |
| WO | 2009/137186 | * 11/2009 |
| WO | 2009135075 | 11/2009 |
| WO | 2010107751 | 9/2010 |
| WO | 2011059565 | 5/2011 |
| WO | 2013063798 | 5/2013 |
| WO | 2013070490 | 5/2013 |
| WO | 2013156038 | 10/2013 |

OTHER PUBLICATIONS

Bu-802a: How Does Rising Internal Resistance Affect Performance? Understanding the Importance of Low Conductivity, Battery University, Available Online at: https://batteryuniversity.com/learn/article/rising_internal_resistance, Accessed from Internet on May 15, 2020,10 pages.
DOE Handbook: Primer on Lead-Acid Storage Batteries, United States Department of Energy, Sep. 1995, 54 pages.
Medical Electrical Equipment—Part 1: General Requirements for Safety, British Standard, BS EN 60601-1:1990-BS5724-1:1989, Mar. 1979, 200 pages.
Summary of Safety and Effectiveness, Medtronic InterStim System for Urinary Control, Apr. 15, 1999, pp. 1-18.
The Advanced Bionics Precision™ Spinal Cord Stimulator System, Advanced Bionics Corporation, Apr. 27, 2004, pp. 1-18.
UL Standard for Safety for Medical and Dental Equipment, Underwriters Laboratories 544, 4th edition, Dec. 30, 1998, 128 pages.
U.S. Appl. No. 14/827,067, Systems and Methods for Neurostimulation Electrode Configurations Based on Neural Localization, filed Aug. 14, 2015, 101 pages.
U.S. Appl. No. 14/827,081, Implantable Lead Affixation Structure for Nerve Stimulation to Alleviate Bladder Dysfunction and Other Indication, filed Aug. 14, 2015, 32 pages.
U.S. Appl. No. 14/827,095, Integrated Electromyographic Clinician Programmer for Use With an Implantable Neurostimulator, filed Aug. 14, 2015, 110 pages.
U.S. Appl. No. 14/827,108, Electromyographic Lead Positioning and Stimulation Titration in a Nerve Stimulation System for Treatment of Overactive Bladder, filed Aug. 14, 2015, 106 pages.
U.S. Appl. No. 14/991,752, Electromyographic Lead Positioning and Stimulation Titration in a Nerve Stimulation System for Treatment of Overactive Bladder, filed Jan. 8, 2016, 104 pages.
U.S. Appl. No. 14/991,784, Methods for Determining Neurostimulation Electrode Configurations Based on Neural Localization, filed Jan. 8, 2016, 99 pages.
U.S. Appl. No. 62/038,131, External Pulse Generator Device and Associated Methods for Trial Nerve Stimulation, filed Aug. 15, 2014, 33 pages.
U.S. Appl. No. 62/041,611, Electromyographic Lead Positioning and Stimulation Titration in a Nerve Stimulation System for Treatment of Overactive Bladder, Pain, and Other Indicators, filed Aug. 25, 2014, 57 pages.
U.S. Appl. No. 62/101,666, Patient Remote and Associated Methods of Use With a Nerve Stimulation System, filed Jan. 9, 2015, 67 pages.
U.S. Appl. No. 62/101,782, Antenna and Methods of Use for an Implantable Nerve Stimulator, filed Jan. 9, 2015, 54 pages.
U.S. Appl. No. 62/101,884, Attachment Devices and Associated Methods of Use With a Nerve Stimulation Charging Device, filed Jan. 9, 2015, 56 pages.
U.S. Appl. No. 62/101,888, Electromyographic Lead Positioning and Stimulation Titration in a Nerve Stimulation System for Treatment of Overactive Bladder, filed Jan. 9, 2015, 106 pages.
U.S. Appl. No. 62/101,897, Systems and Methods for Neurostimulation Electrode Configurations Based on Neural Localization, filed Jan. 9, 2015, 103 pages.
U.S. Appl. No. 62/101,899, Integrated Electromyographic Clinician Programmer for Use With an Implantable Neurostimulator, filed Jan. 9, 2015, 104 pages.
U.S. Appl. No. 62/191,134, Implantable Nerve Stimulator Having Internal Electronics Without Asic and Methods of Use, filed Jul. 10, 2015, 60 pages.
Barnhart et al., A Fixed-Rate Rechargable Cardiac Pacemaker, Applied Physics Laboratory Technical Digest, Jan.-Feb. 1970, pp. 2-9.
Benditt et al., A Combined Atrial/Ventricular Lead for Permanent Dual-Chamber Cardiac Pacing Applications, Chest, vol. 83, No. 6, Jun. 1983, pp. 929-931.
Bosch et al., Sacral (S3) Segmental Nerve Stimulation as a Treatment for Urge Incontinence in Patients with Detrusor Instability: Results of Chronic Electrical Stimulation Using an Implantable Neural Prosthesis, The Journal of Urology, vol. 154, No. 2, Aug. 1995, pp. 504-507.
Boyce et al., Research Related to the Development of an Artificial Electrical Stimulator for the Paralyzed Human Bladder: A Review, The Journal of Urology, vol. 91, No. 1, Jan. 1964, pp. 41-51.
Bradley et al., Further Experience with the Radio Transmitter Receiver Unit for the Neurogenic Bladder, Journal of Neurosurgery, vol. 20, No. 11, Nov. 1963, pp. 953-960.
Broggi et al., Electrical Stimulation of the Gasserian Ganglion for Facial Pain: Preliminary Results, Acta Neurochirurgica, vol. 39, 1987, pp. 144-146.
Cameron et al., Effects of Posture on Stimulation Parameters in Spinal Cord Stimulation, Neuromodulation, vol. 1, No. 4, Oct. 1998, pp. 177-183.
Chartier-Kastler, Sacral Neuromodulation for Treating the Symptoms of Overactive Bladder Syndrome and Non-Obstructive Urinary Retention:>10years of Clinical Experience, Journal Compilation, BJU international, vol. 101, 2007, pp. 417-423.
Connelly et al., Atrial Pacing Leads Following Open Heart Surgery: Active or Passive Fixation?, Pacing and Clinical Electrophysiology, vol. 20, No. 10, Oct. 1997, pp. 2429-2433.

(56) References Cited

OTHER PUBLICATIONS

Fischell, The Development of Implantable Medical Devices at the Applied Physics Laboratory, Johns Hopkins Applied Physics Laboratory Technical Digest, vol. 13 No. 1, 1992, pp. 233-243.

Gaunt et al., Control of Urinary Bladder Function with Devices: Successes and Failures, Progress in Brain Research, vol. 152, 2006, pp. 1-24.

Ghovanloo et al., A Small Size Large Voltage Compliance Programmable Current Source for Biomedical Implantable Microstimulators, Proceedings of the 25th Annual International Conference of the Institute of Electrical and Electronics Engineers, Engineering in Medicine and Biology Society, Sep. 17-21, 2003, pp. 1979-1982.

Helland, Technical Improvements to be Achieved by the Year 2000: Leads and Connector Technology, Rate Adaptive Cardiac Pacing, Springer Verlag, 1993, pp. 279-292.

Hidefjall, The Pace of Innovation—Patterns of Innovation in the Cardiac Pacemaker Industry, Linkoping University Press, 1997, 398 pages.

Ishihara et al., A Comparative Study of Endocardial Pacemaker Leads, Cardiovascular Surgery, Nagoya Ekisaikai Hospital, 1st Department of Surgery, Nagoya University School of Medicine, 1981, pp. 132-135.

Jonas et al., Studies on the Feasibility of Urinary Bladder Evacuation by Direct Spinal Cord Stimulation. I. Parameters of Most Effective Stimulation, Investigative Urology, vol. 13, No. 2, 1975, pp. 142-150.

Kakuta et al., In Vivo Long Term Evaluation of Transcutaneous Energy Transmission for Totally Implantable Artificial Heart, American Society for Artificial Internal Organs Journal, Mar.-Apr. 2000, pp. 1-2.

Kester et al., Voltage-To-Frequency Converters, 2009, Available Online at: https://www.analog.com/media/on/training-seminars/tutorials/MT-028.pdf, 7 pages.

Lazorthes et al., Chronic Stimulation of the Gasserian Ganglion for Treatment of Atypical Facial Neuralgia, Pacing and Clinical Electrophysiology, vol. 10, Jan.-Feb. 1987, pp. 257-265.

Lewis et al., Early Clinical Experience with the Rechargeable Cardiac Pacemaker, The Annals of Thoracic Surgery, vol. 18, No. 5, Nov. 1974, pp. 490-493.

Love et al., Experimental Testing of a Permanent Rechargeable Cardiac Pacemaker, The Annals of Thoracic Surgery, vol. 17, No. 2, Feb. 1, 1974, pp. 152-156.

Love, Pacemaker Troubleshooting and Follow-up, Clinical Cardiac Pacing, Defibrillation, and Resynchronization Therapy, Chapter 24, 2007, pp. 1005-1062.

Madigan et al., Difficulty of Extraction of Chronically Implanted Tined Ventricular Endocardial Leads, Journal of the American College of Cardiology, vol. 3, No. 3, Mar. 1984, pp. 724-731.

Meglio, Percutaneously Implantable Chronic Electrode for Radiofrequency Stimulation of the Gasserian Ganglion. A Perspective in the Management of Trigeminal Pain, Acta Neurochirurgica, vol. 33, 1984, pp. 521-525.

Meyerson, Alleviation of Atypical Trigeminal Pain by Stimulation of the Gasserian Ganglion via an Implanted Electrode, Acta Neurochirurgica Supplementum, vol. 30, 1980, pp. 303-309.

Mitamura et al., Development of Transcutaneous Energy Transmission System, Available Online at: https://link.springer.com/chapter/10.1007/978-4-431-65964-8_28, Jan. 1988, pp. 265-270.

Nakamura et al., Biocompatibility and Practicality Evaluations of Transcutaneous Energy Transmission Unit for the Totally Implantable Artifical Heart System, Journal of Artificial Organs, vol. 27, No. 2, 1998, pp. 347-351.

Nashold et al., Electromicturition in Paraplegia. Implantation of a Spinal Neuroprosthesis, Archives of Surgery., vol. 104, Feb. 1972, pp. 195-202.

Painter et al., Implantation of an Endocardial Tined Lead to Prevent Early Dislodgement, The Journal of Thoracic and Cardiovascular Surgery, vol. 77, No. 2, Feb. 1979, pp. 249-251.

Perez, Lead-Acid Battery State of Charge Vs. Voltage, Available Online at: https://www.scubaengineer.com/documents/lead_acid_battery_charging_graphs.pdf, Aug.-Sep. 1993, 5 pages.

Schaldach et al., A Long-Lived, Reliable, Rechargeable Cardiac Pacemaker, Advances in Pacemaker Technology Engineering in Medicine, vol. 1, 1975, 34 pages.

Scheuer-Leeser et al., Polyurethane Leads: Facts and Controversy, Pacing and Clinical Electrophysiology, vol. 6, Mar. 1983, pp. 454-458.

Smith, Changing Standards for Medical Equipment UL 544 and UL 187 Vs. UL 2601, Biomedical Safety & Standards, vol. 32, No. 9, May 15, 2002, 8 pages.

Tanagho et al., Bladder Pacemaker: Scientific Basis and Clinical Future, Urology, vol. 20, No. 6, Dec. 1982, pp. 614-619.

Tanagho, Neuromodulation and Neurostimulation: Overview and Future Potential, Translational Andrology and Urology, vol. 1, No. 1, 2012, pp. 44-49.

Torres et al., Electrostatic Energy-Harvesting and Battery-Charging CMOS System Prototype, Institute of Electrical and Electronics Engineers Transactions on Circuits and Systems I: Regular Papers, vol. 56, No. 9, Dec. 22, 2008, 10 pages.

Young, Electrical Stimulation of the Trigeminal Nerve Root for the Treatment of Chronic Facial Pain, Journal of Neurosurgery, vol. 83, No. 1, Jul. 1995, 11 pages.

\* cited by examiner

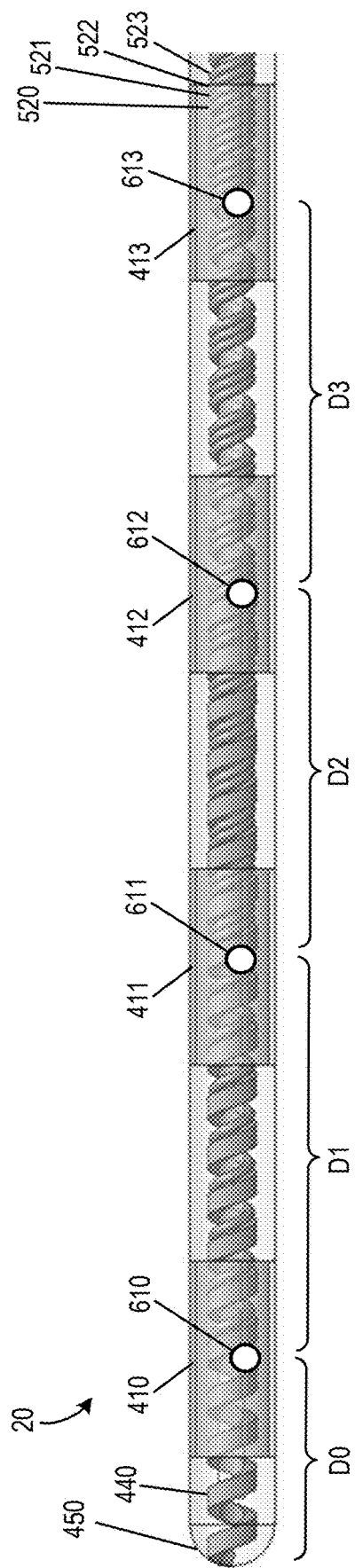
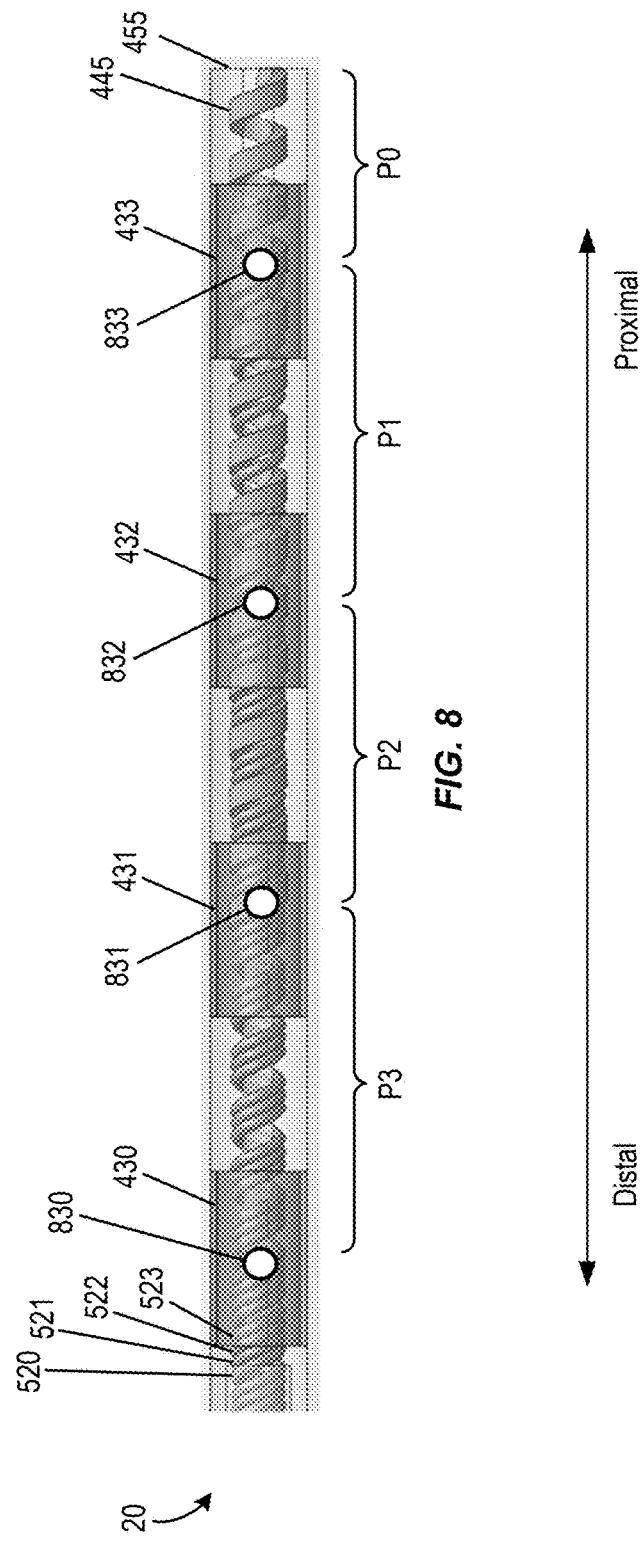
FIG. 7
FIG. 8

900

| 910 | Provide a flexible tubular member from a first electrically nonconductive material, wherein the tubular member comprises a distal portion and a proximal portion, and wherein the tubular member comprises one or more distal apertures at the distal portion of the tubular member and one or more proximal apertures at the proximal portion of the tubular member |

↓

| 920 | Dispose one or more conductors around an elongate mandrel in a coiled manner |

↓

| 930 | Place the elongate mandrel within an interior of the tubular member |

↓

| 940 | Mount one or more electrodes along an exterior of the distal portion of the tubular member, the electrodes comprising a first electrically conductive material |

↓

| 950 | Mount one or more connector interfaces along an exterior of the proximal portion of the tubular member, the connector interfaces comprising a second electrically conductive material |

↓

| 960 | For each conductor, causing a distal end of the conductor to exit the distal portion of the tubular member via a respective distal aperture to couple with a respective electrode, and causing a proximal end of the conductor to exit the proximal portion of the tubular member via a respective proximal aperture to couple with a respective connector interface |

↓

| 970 | Insert or inject a first filler element into the interior of the tubular member to occupy at least a portion of one or more gaps in the interior of the tubular member resulting from the exit of one or more of the one or more conductors from the tubular member, wherein the first filler element comprises a second electrically nonconductive material |

↓

| 980 | Cause at least the first electrically nonconductive material to reflow and set so as to secure at least a portion of the one or more conductors and the first filler element within the tubular member |

↓

| 990 | Remove the elongate mandrel. |

*FIG. 9*

NEUROSTIMULATION LEADS WITH REDUCED CURRENT LEAKAGE

CROSS-REFERENCES TO RELATED APPLICATIONS

This application claims the benefit of U.S. Provisional Application No. 63/068,299, entitled "NEUROSTIMULATION LEADS WITH REDUCED CURRENT LEAKAGE", and filed Aug. 20, 2020, the entirety of which is incorporated by reference herein.

RELATED FIELD

The present invention relates to leads for medical devices, and in particular neurostimulation leads, and methods of manufacturing such leads.

BACKGROUND

Treatments with neurostimulation systems have become increasingly common in recent years. These neurostimulation systems generally have a neurostimulation component (for example, a pulse generator) and one or more interfacing components. The pulse generator may be an implantable pulse generator (IPG) or an external pulse generator (EPG). The interfacing components may include a neurostimulator programmer, which may be a clinician programmer (CP) or a patient remote for example. The neurostimulator programmer may be able to, for example, adjust stimulation parameters, turn stimulation on or off, receive stimulation history from the pulse generator, and/or transmit programming instructions to the pulse generator.

While neurostimulation systems have been widely implemented in treating a number of conditions, various aspects of neurostimulation systems can be improved. One common issue with implanted neurostimulation systems is current leakage from stimulation electrodes of leads as electricity is delivered through the electrodes. Ideally, the actively stimulating electrodes of a lead would deliver to the targeted tissue exactly the amount of electrical current that is transmitted to them by a pulse generator. However, for various reasons such as those explained herein, conditions are often not ideal in the context of implantable leads, particularly when the leads are implanted for extended periods in an environment including fluid (e.g., body fluid). Implantation in such an environment may result in current leakage when electrodes are actively stimulating. Too much current leakage can be problematic, especially over time. For example, increased current leakage over a period of time may require an inordinate number of recalibrations to effectuate a prescribed stimulation therapy. These recalibrations may require additional energy output by a pulse generator, which may reduce battery life of the pulse generator. In order to minimize these issues, there is an outstanding need for leads that reduce current leakage.

BRIEF SUMMARY

This disclosure generally relates to neurostimulation treatment systems and associated devices and methods, and in particular to reducing current leakage in neurostimulation leads. The embodiments described herein have particular application to sacral nerve stimulation treatment systems configured to treat bladder and bowel related dysfunctions (e.g., inflammatory bowel diseases). It will be appreciated, however, that the present invention may also be utilized for the treatment of pain, or any other suitable indications, such as movement or affective disorders, as will be appreciated by one of skill in the art.

A common issue with implanted neurostimulation systems is current leakage from stimulation electrodes of leads. This may occur, for example, as electricity is delivered through the electrodes. Neurostimulation leads may include a lead body along which one or more electrodes are secured. The electrodes may be coupled to terminals of a pulse generator (e.g., an IPG, an EPG) via one or more conductors that extend along and within a length of the lead body. In some embodiments, current leakage may in part be due to the migration of body fluid into the lead body over time, creating a conductive internal path between electrodes or conductors of the lead. In some embodiments, the conductors of the lead body, which are disposed within an interior of the lead body, are electrically coupled with electrodes of the lead body, which are disposed along an exterior of the lead body. In order to achieve this coupling, the lead body needs to have one or more exit sites allowing the conductors to couple with the electrodes. These exit sites may provide paths for ingress of body fluids from the surrounding environment of the implant location where the lead is secured. These body fluids include electrolytes, and as such, could serve as a pathway for current to leak by conducting away from the intended target (e.g., nerve tissue external to the lead body) and toward the interior of the lead. This may create an alternative or additional current pathway within the interior of the lead between electrodes. Neurostimulation systems are often implanted for extended periods of time, and this current leakage may increase and compound over time as increasing amounts of body fluid migrate into the lead body.

As a result, periodic recalibrations may be required to effectuate optimal therapy at prescribed stimulation levels. For example, electrical output by an electrode may need to be increased to accommodate for current leakage so as to achieve a prescribed stimulation level. Frequent recalibration can prove to be an inconvenience for patients. The need for frequent recalibration may also result in noncompliance from some patients, thereby reducing the efficacy of neurostimulation for this patient. Additionally, the recalibrations typically increase the required energy output by a pulse generator, which may reduce battery life of the pulse generator. This may be especially problematic in an implantable pulse generator (IPG) with a nonrechargeable battery (e.g., requiring surgery for replacement of the battery), but it is also an issue with an IPG having a rechargeable battery (e.g., requiring more frequent charging of the battery). Similarly, current leakage also affects external pulse generators (EPGs), which would need to have batteries replaced or recharged more frequently than would be optimal.

To address these issues, disclosed herein are implantable neurostimulation leads that, among other things, reduces current leakage by minimizing or preventing the ingress of body fluids into the lead body, and methods of manufacturing such a lead.

In some embodiments, an implantable neurostimulation lead includes a lead body having a proximal portion and a distal portion, wherein the lead body has one or more proximal apertures along the proximal portion and one or more distal apertures along the distal portion; a lumen extending through the lead body; one or more electrodes along an exterior of the lead body at the distal portion of the lead body; one or more connector interfaces along the exterior of the lead body at the proximal portion of the lead body, each connector interface configured to engage with a respective connector of a pulse generator; one or more conductors extending through an interior of the lead body, each of the conductors having a proximal end and a distal end, wherein the proximal end exits the interior of the lead body via a respective proximal aperture to couple with a respective connector interface, and wherein the distal end exits the interior of the lead body via a respective distal aperture to couple with a respective electrode, each conductor coupling a respective electrode with a respective connector interface; and a first filler element configured to occupy at least a portion of one or more gaps in the interior of the lead body resulting from the exit of one or more of the one or more conductors from the lead body, wherein the first filler element comprises an electrically nonconductive material.

In some embodiments, the one or more conductors are coiled around the lumen, and wherein the first filler element is coiled around the lumen. In some embodiments, the one or more conductors are coiled around the lumen at a first pitch, and wherein the first filler element is coiled around the lumen at a second pitch, the second pitch substantially the same as the first pitch. In some embodiments, the one or more conductors are coiled around the lumen at a first pitch, and wherein the first filler element is coiled around the lumen at a second pitch, the second pitch being different from the first pitch.

In some embodiments, the first filler element comprises a multi-filar structure. In some embodiments, the one or more electrodes comprises four electrodes and the one or more connector interfaces comprises four connector interface, and wherein the multi-filar structure comprises three filars. In some embodiments, the one or more electrodes comprises a first electrode and a second electrode; and the one or more conductors comprises a first conductor and a second conductor, wherein a distal end of the first conductor exits the interior of the lead body via a first distal aperture and a distal end of the second conductor exits the interior of the lead body via a second distal aperture, the first distal aperture being distal to the second distal aperture; wherein a first filar of the multi-filar structure is sized to extend between a distal location along the interior of the lead body to the first distal aperture, and wherein a second filar of the multi-filar structure is sized to extend between the distal location to the second distal aperture.

In some embodiments, the one or more connector interfaces comprises a first connector interface and a second connector interface; and the one or more conductors comprises a first conductor and a second conductor, wherein a proximal end of the first conductor exits the interior of the lead body via a first proximal aperture and a proximal end of the second conductor exits the interior of the lead body via a second proximal aperture, the first proximal aperture being distal to the second proximal aperture; wherein a first filar of the multi-filar structure is sized to extend between a proximal location along the interior of the lead body to the first proximal aperture, and wherein a second filar of the multi-filar structure is sized to extend between the proximal location to the second proximal aperture.

In some embodiments, the first filler element is disposed at the distal portion of the lead. In some embodiments, the first filler element is disposed at the distal portion of the lead, and a second filler element is disposed at the proximal portion of the lead, the second filler element comprising an electrically nonconductive material.

In some embodiments, the first filler element comprises a polymer material. In some embodiments, the first filler element comprises a polyurethane material. In some embodiments, the lead body comprises a polymer material. In some embodiments, the lead body comprises a polyurethane material In some embodiments, the first filler element comprises a solid extrusion. In some embodiments, the first filler element comprising an adhesive (e.g., polyurethane adhesive) or cured thermoplastic or thermoset polymer material that is configured to be injected into the at least one or more gaps in the interior or lumen of the lead body (e.g., viscous liquid that is heat or ultraviolet (UV) cured).

In some embodiments, the first filler element comprises a filar having a length of 10 to 60 mm. In some embodiments, the first filler element comprises a filar having a diameter of 0.03 to 0.3 mm. In some embodiments, the first filler element comprises a ribbon-like filar having a width of 0.01 to 2 mm.

Methods for manufacturing implantable neurostimulation leads are disclosed herein. Such a method includes providing a flexible tubular member from a first electrically nonconductive material, wherein the tubular member comprises a distal portion and a proximal portion, and wherein the tubular member comprises one or more distal apertures at the distal portion of the tubular member and one or more proximal apertures at the proximal portion of the tubular member; disposing one or more conductors around an elongate mandrel in a coiled manner; placing the elongate mandrel within an interior of the tubular member; mounting one or more electrodes along an exterior of the distal portion of the tubular member, the electrodes comprising a first electrically conductive material; mounting one or more connector interfaces along an exterior of the proximal portion of the tubular member, the connector interfaces comprising a second electrically conductive material; for each conductor, causing a distal end of the conductor to exit the distal portion of the tubular member via a respective distal aperture to couple with a respective electrode, and causing a proximal end of the conductor to exit the proximal portion of the tubular member via a respective proximal aperture to couple with a respective connector interface; inserting or injecting a first filler element into the interior of the tubular member to occupy at least a portion of one or more gaps in the interior of the tubular member resulting from the exit of one or more of the one or more conductors from the tubular member, wherein the first filler element comprises a second electrically nonconductive material; and removing the elongate mandrel.

In some embodiments, disposing one or more conductors around the elongate mandrel in a coiled manner comprises coiling the one or more conductors around the elongate mandrel at a first pitch. In some embodiments, inserting or injecting the first filler element into the interior of the tubular member comprises coiling the first filler element around the elongate mandrel at a second pitch, the second pitch substantially the same as the first pitch. In some embodiments, inserting or injecting the first filler element into the interior of the tubular member comprises coiling the first filler element around the elongate mandrel at a second pitch, the second pitch different from the first pitch.

In some embodiments, the one or more conductors are pre-coiled, and wherein disposing one or more conductors around the elongate mandrel in a coiled manner comprises sliding the pre-coiled conductors over the elongate mandrel. In some embodiments, the first filler element is pre-coiled, and wherein inserting or injecting the first filler element into the interior of the tubular member comprises sliding the pre-coiled filler element over the elongate mandrel.

In some embodiments, the first filler may comprise a solid extrusion, wherein inserting or injecting comprises inserting the solid extrusion into the interior of the tubular body and the method further comprises securing at least a portion of the one or more conductors and the solid extrusion within the tubular member. In some embodiments, securing may further include causing at least the first electrically nonconductive material to reflow and set so as to secure at least a portion of the one or more conductors and the first filler element within the tubular member.

In some embodiments, the first filler element may comprise an adhesive or cured thermoplastic or thermoset polymer material, wherein inserting or injecting comprises injecting the polymer material into the interior of the tubular body so as to form a seal to secure at least a portion of the one or more conductors and the first filler element within the tubular member.

In some embodiments, the one or more electrodes comprises a first electrode and a second electrode, and wherein the one or more connector interfaces comprises a first connector interface and a second connector interface. In these embodiments, the method may further include placing a first spacer in between the first electrode and the second electrode; placing a second spacer in between the first connector interface and the second connector interface, wherein the first spacer and the second spacer comprise a third electrically nonconductive material; and causing the third electrically nonconductive material to reflow and set so as to seal the one or more distal apertures and the one or more proximal apertures around the distal and proximal ends of the one or more conductors. In some embodiments, the first electrically nonconductive material and the third electrically nonconductive material are substantially the same. In some embodiments, the first electrically nonconductive material, the second electrically nonconductive material, and the third electrically nonconductive material are substantially the same. In some embodiments, the first electrically nonconductive material, the second electrically nonconductive material, and the third electrically nonconductive material comprise a polyurethane material.

In some embodiments, the first filler element is a multifilar structure. In these embodiments, inserting or injecting the first filler element into the interior of the tubular member comprises: inserting a first filar into the interior of the tubular member; and inserting a second filar into the interior of the tubular member. Multiple filars may allow for granularity in varying the size of the filler element along the lead body. As many filars may be inserted as necessary to achieve the desired granularity in size variance.

In some embodiments, the first electrically nonconductive material comprises a polymer material. In some embodiments, the first electrically nonconductive material comprises a polyurethane material. In some embodiments, the first electrically nonconductive material and the second electrically nonconductive material are substantially the same. In some embodiments, the first electrically nonconductive material and the second electrically nonconductive material comprise a polyurethane material.

In some embodiments, the method may further include welding the distal end of the conductor to one or more respective electrodes; and welding the proximal end of the conductor to one or more respective connector interfaces. In some embodiments, the method may further include forming the one or more distal apertures and the one or more proximal apertures by creating slits in the tubular member.

In some embodiments, the first filler element is inserted or injected at the distal portion of the tubular member, and wherein the method further comprises inserting or injecting a second filler element at the proximal portion of the tubular member, the second filler element comprising a fourth electrically nonconductive material. In some embodiments, the method may further include removing excess material in the interior of the tubular member, on the exterior of the tubular member, or an exterior of the one or more electrodes by machining, grinding, or polishing subsequently to incorporating the first filler element into the lumen of the tubular member.

Methods for manufacturing an implantable neurostimulation lead may also include incorporating a filler element into an interior of a flexible tubular member to occupy at least a portion of one or more gaps in the interior of the tubular member resulting from an exit of one or more conductors from the tubular member via a respective distal aperture to couple with a respective electrode. The flexible tubular member may comprise a first electrically nonconductive material and the filler element comprises a second electrically nonconductive material. In some embodiments, the first electrically nonconductive material and the second electrically nonconductive material comprise a polyurethane material.

In some embodiments, incorporating may comprise inserting, injecting, molding (e.g., injection molding, blow molding, or compression molding), machining, 2D printing, 3D printing, melt extruding, solid-state forming, casting, vacuum forming, or coating the filler element into the interior of the flexible tubular member.

BRIEF DESCRIPTION OF THE DRAWINGS

FIG. 7 illustrates an example embodiment of the lead with a filler element at the distal end of the lead.

FIG. 8 illustrates an example embodiment of the lead with a filler element at the proximal end of the lead.

FIG. 9 illustrates an example method of manufacturing a neurostimulation lead.

DETAILED DESCRIPTION

Figure 1:
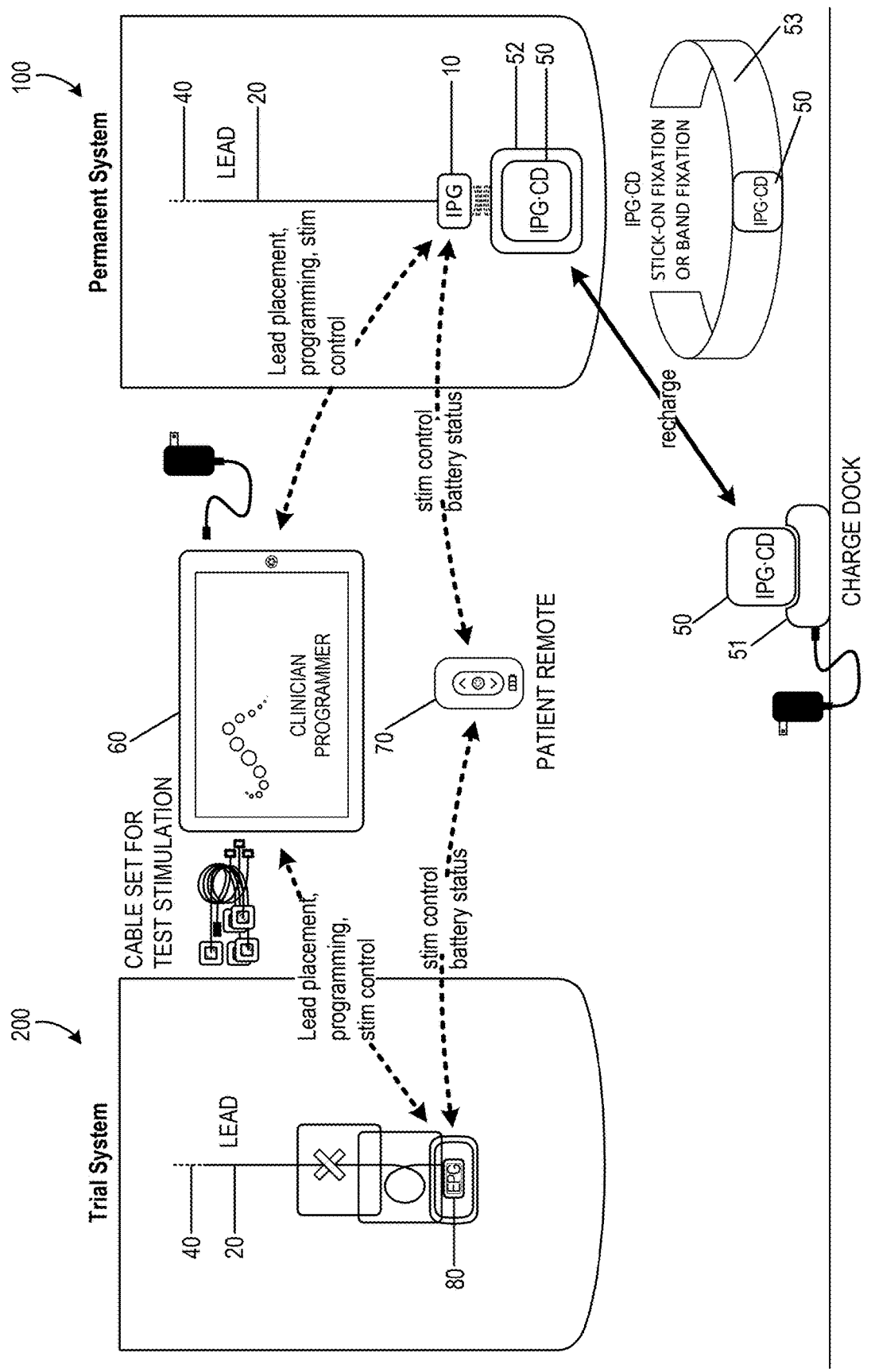
FIG. 1 schematically illustrates a nerve stimulation system, which includes a clinician programmer and a patient remote used in positioning and/or programming of both a trial neurostimulation system and a permanently implanted neurostimulation system.

The present disclosure relates to neurostimulation treatment systems and associated devices, as well as methods of manufacturing such treatment systems. The disclosed systems may in some embodiments relate to sacral nerve stimulation treatment systems configured to treat bladder and bowel dysfunctions, including overactive bladder ("OAB") as well as fecal dysfunctions, and relieve symptoms associated therewith. It will be appreciated, however, that the disclosed systems may also be utilized for any variety of neuromodulation uses, such as fecal dysfunction, the treatment of pain, or any other suitable indications, such as movement or affective disorders, as will be appreciated by one of skill in the art.

I. Neurostimulation Indications

Neurostimulation (or neuromodulation, as may be used interchangeably hereunder) treatment systems, such as any of those described herein, can be used to treat a variety of ailments and associated symptoms, such as acute pain disorders, movement disorders, affective disorders, as well as bladder related dysfunction and fecal dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include, but are not limited to, OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

II. Sacral Neuromodulation (SNM) Overview

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

III. Example Systems

FIG. 1 schematically illustrates example nerve stimulation system setups, which includes a setup for use in a trial neurostimulation system 200 and a setup for use in a permanently implanted neurostimulation system 100, in accordance with aspects of the invention. The EPG 80 and IPG 10 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP 60 is also able to save and display previous (e.g., up to the last four) programs that were used by a patient to help facilitate re-programming. In some embodiments, the CP 60 further includes a USB port for saving reports to a USB drive and a charging port. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve. In various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2:
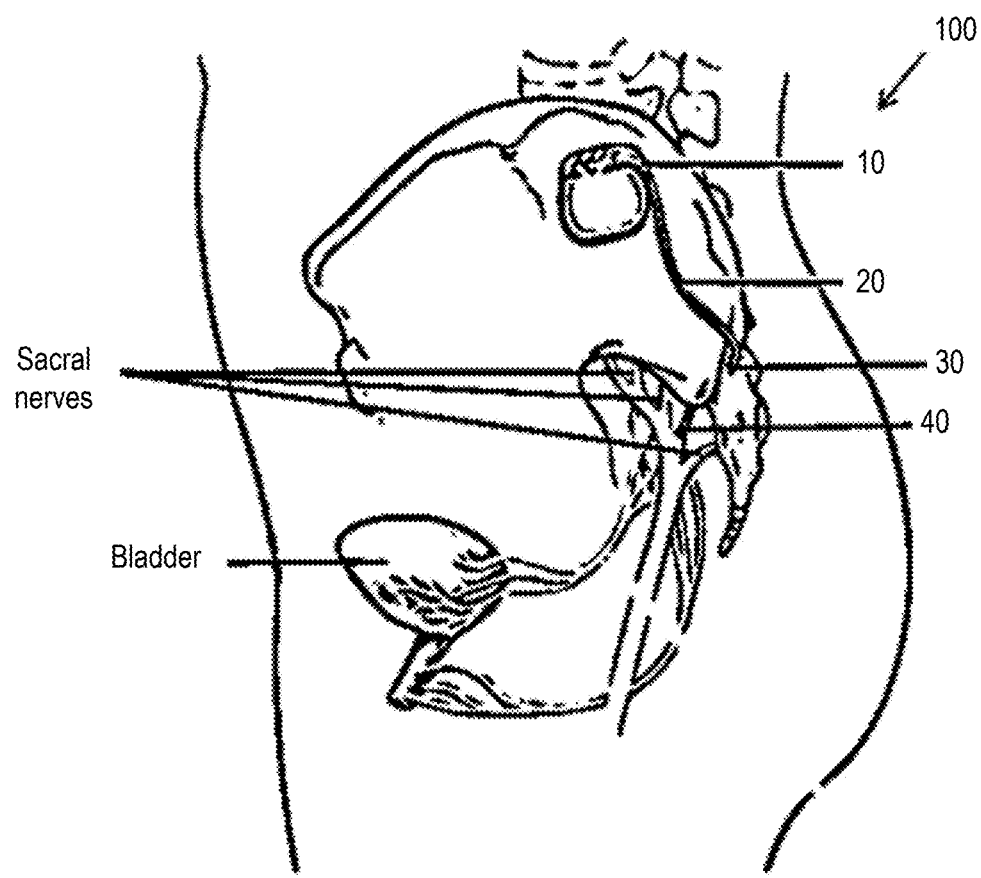
FIG. 2 illustrates an example of a fully implanted neurostimulation system.

FIG. 2 schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Figure 3:
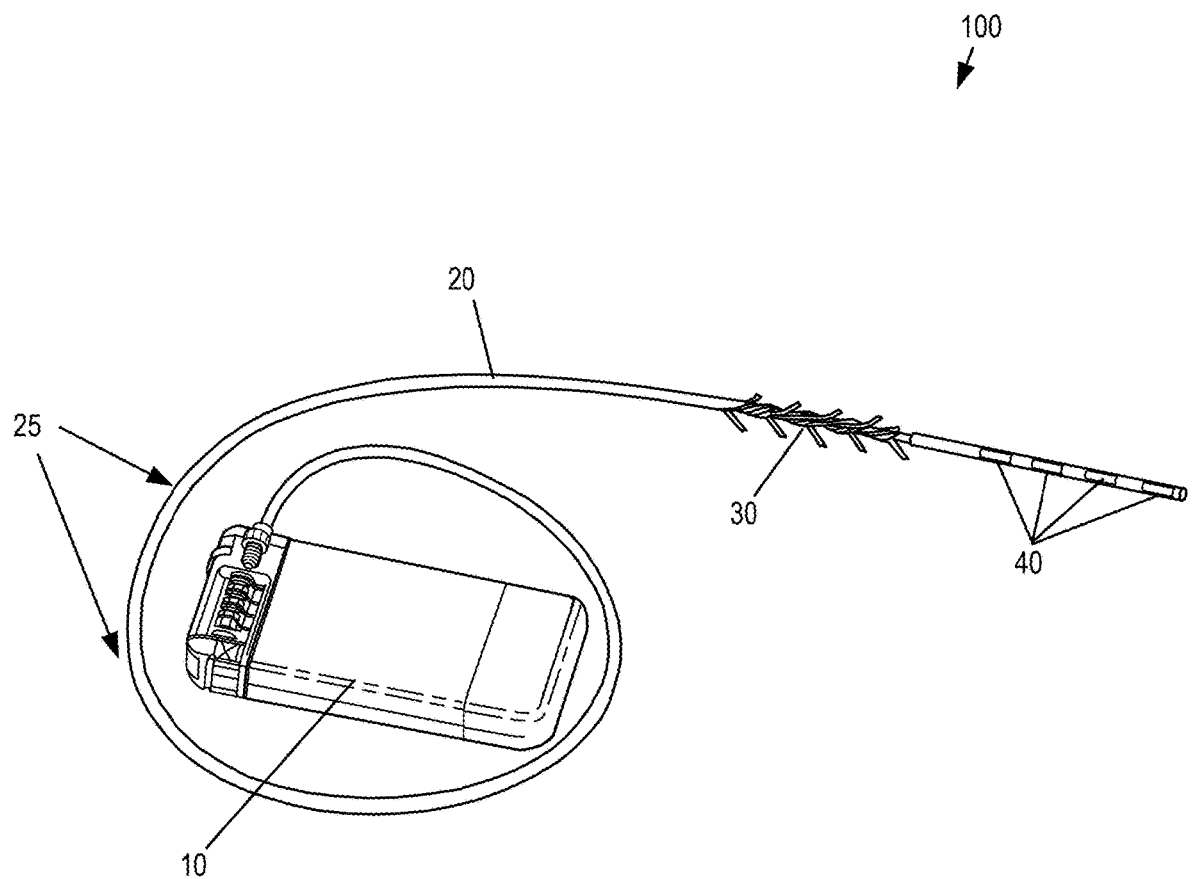
FIG. 3 illustrates an example of a neurostimulation system having an implantable stimulation lead, an implantable pulse generator, and an external charging device.

FIG. 3 illustrates an example neurostimulation system 100 that is fully implantable and adapted for sacral nerve stimulation treatment. The implantable system 100 includes an IPG 10 that is coupled to an implantable neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The neurostimulation lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

Figure 4:
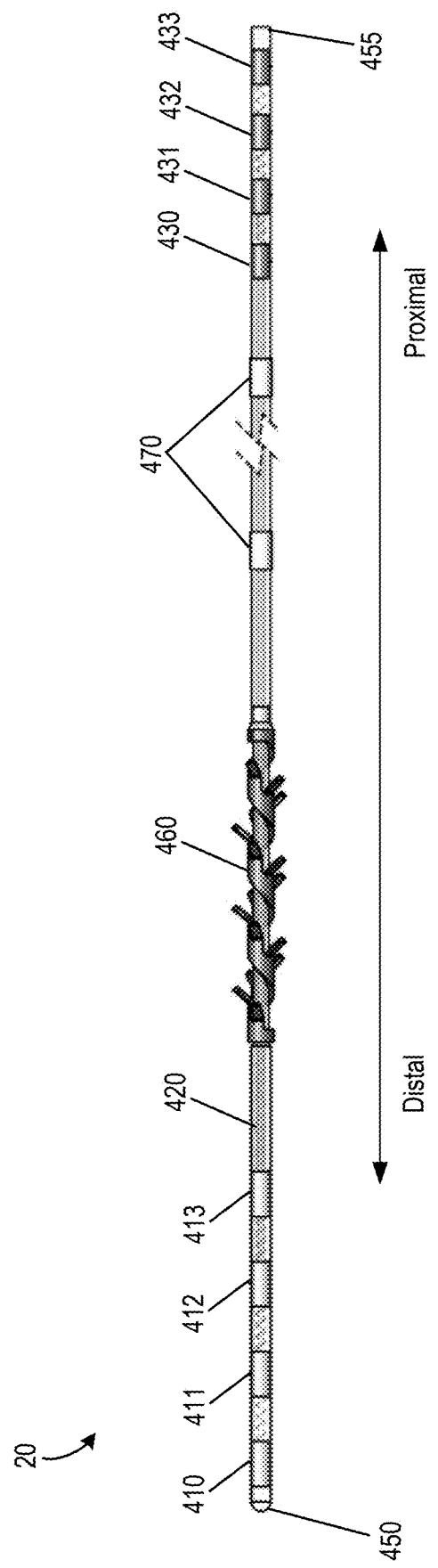
FIG. 4 illustrates an example lead of a neurostimulation system.

FIG. 4 illustrates an example lead 20 of a neurostimulation system 100. In some embodiments, an implantable neurostimulation lead (e.g., referencing FIG. 4, the lead 20) may include a lead body having a proximal portion and a distal portion. In some embodiments, the lead 20 may be securable to a desired location within the body using a lead anchor 460. The lead anchor 460 may be an integrated anchor that is part of the lead body of the lead 20, or alternatively may be a separate element that is coupleable to the lead 20. In some embodiments, the neurostimulation lead may include one or more electrodes along an exterior of the lead body at the distal portion of the lead body. For example, referencing FIG. 4, the lead 20 includes four electrodes 410, 411, 412, and 413. In this example, the most distal electrode 410 is proximal to the distal end of the lead body (the distal tip 450). The distal tip 450 may be composed of an electrical insulator. Such a configuration may be advantageous in localizing the electrical current delivered by the most distal electrode 410, since the insulated distal tip 450 may reduce or prevent conduction of electrical current along a distal direction beyond the most distal electrode 410. However, the disclosure contemplates that the most distal electrode may alternatively be at the distal end of the lead body. The electrodes may be composed of one or more electrically conductive materials, such as a suitable metal, and may thus act as electrical conductors for stimulating, for example, nerve tissue at a target location.

In some embodiments, the neurostimulation lead 20 may include one or more connector interfaces along the exterior of the lead body at the proximal portion of the lead body. For example, referencing FIG. 4, the lead 20 includes four connector interfaces 430, 431, 432, and 433. In this example, the most proximal connector interface 433 is distal to the proximal end of the lead body (the proximal tip 455). However, the disclosure contemplates that the most proximal electrode may alternatively be at the proximal end of the lead body. Each of these connector interfaces may be configured to engage with a respective connector of a pulse generator. The connectors of the pulse generator may in turn be electrically coupled to the circuitry that is capable of providing an electrical current. Similar to the electrodes, the connector interfaces may be composed of one or more electrically conductive materials, such as a suitable metal, so that they may receive and conduct electrical current from the connectors. Although the disclosure focuses on example leads with four electrodes and four connector interfaces, the disclosure contemplates any number suitable of electrodes and connector interfaces.

In some embodiments, the neurostimulation lead may include one or more conductors extending through an interior of the lead body, each of the conductors having a proximal end and a distal end. The conductors may be made of electrically conductive material, and may couple the electrodes to the connector interfaces. In some embodiments, the distal ends of the conductors may be directly coupled to the electrodes, and the proximal ends of the conductors may be directly coupled to the connector interfaces. For example, referencing FIG. 4, a plurality of conductors 420 may be directly coupled to the electrodes 410, 411, 412, and 413 at the distal ends, and may be directly coupled to the connector interfaces 430, 431, 432, and 433 at their proximal ends. In some embodiments, the conductors may not be coupled directly to the electrodes or connector interfaces, and may instead have one or more intermediary components that electrically couple the conductors to the electrodes or connector interfaces. In some embodiments, each conductor may be electrically insulated from the other conductors (if any), such that connector interfaces are electrically coupled only to respective one or more electrodes. For example, referencing FIG. 4, the plurality of conductors 420 may include four separate conductors that are electrically insulated from each other such that the connector interface 430 is electrically coupled only to the electrode 410, the connector interface 431 is coupled only to the electrode 411, the connector interface 432 is coupled only to the electrode 412, and the connector interface 433 is coupled only to the electrode 413. As another example, a connector interface may be coupled to multiple electrodes (e.g., a single connector interface may be coupled to two electrodes). As another example, an electrode may be coupled to multiple connector interfaces (e.g., a single electrode may be coupled to two connector interfaces).

Figure 5:
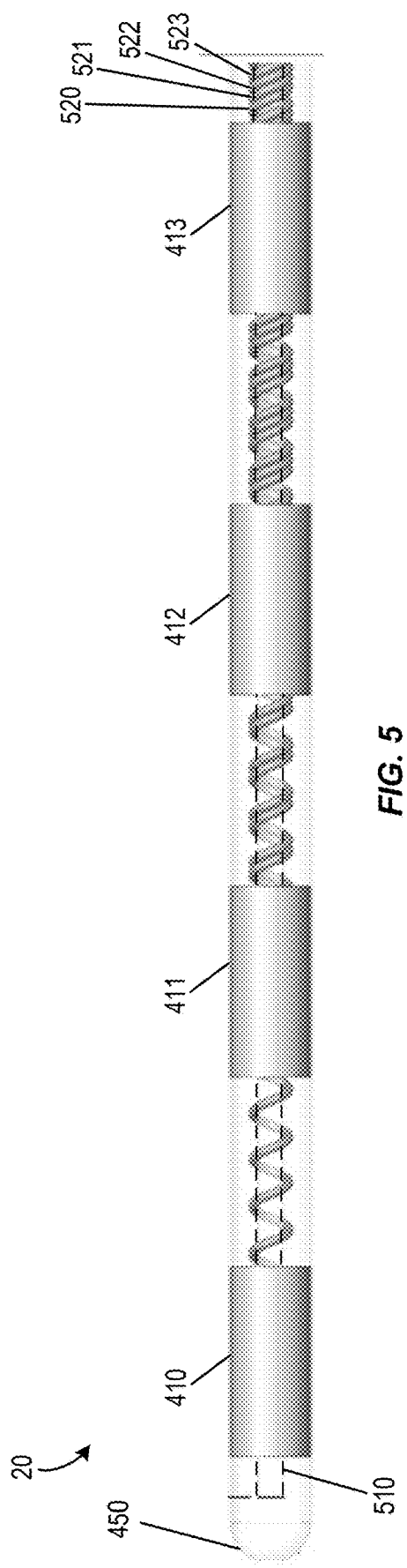
FIG. 5 illustrates a close-up view of a distal portion of the lead.

FIG. 5 illustrates a close-up view of a distal portion of the lead 20. In some embodiments, the neurostimulation lead may include a lumen extending through the lead body. For example, referencing FIG. 5, the lead 20 includes a lumen 510 that extends through the lead body. In the illustrated example, the lumen terminates before the distal tip 450 of the lead 20. This lumen may be configured to be able to receive a stylet during the implantation procedure, so that the lead body is afforded sufficient stiffness so as to enable a physician to maneuver the lead body. In some embodiments, the one or more conductors may extend within the lumen. In other embodiments, the one or more conductors may be coiled around the lumen. Referencing FIG. 5, four conductors 520, 521, 522, and 523 are coiled around the lumen 510, each conductor coupled to a respective electrode at the distal end and further coupled to a respective connector interface at the proximal end (not illustrated). In some embodiments, the coiled conductors may be interleaved (e.g., as illustrated in FIG. 5).

In some embodiments, the conductors may be touching each other but still electrically insulated from each other. For example, individual conductors may be surrounded by an electrically insulative coating. Referencing the example illustrated in FIG. 5, the interleaved coiled conductors are catching but nonetheless insulated from each other.

Figure 6:
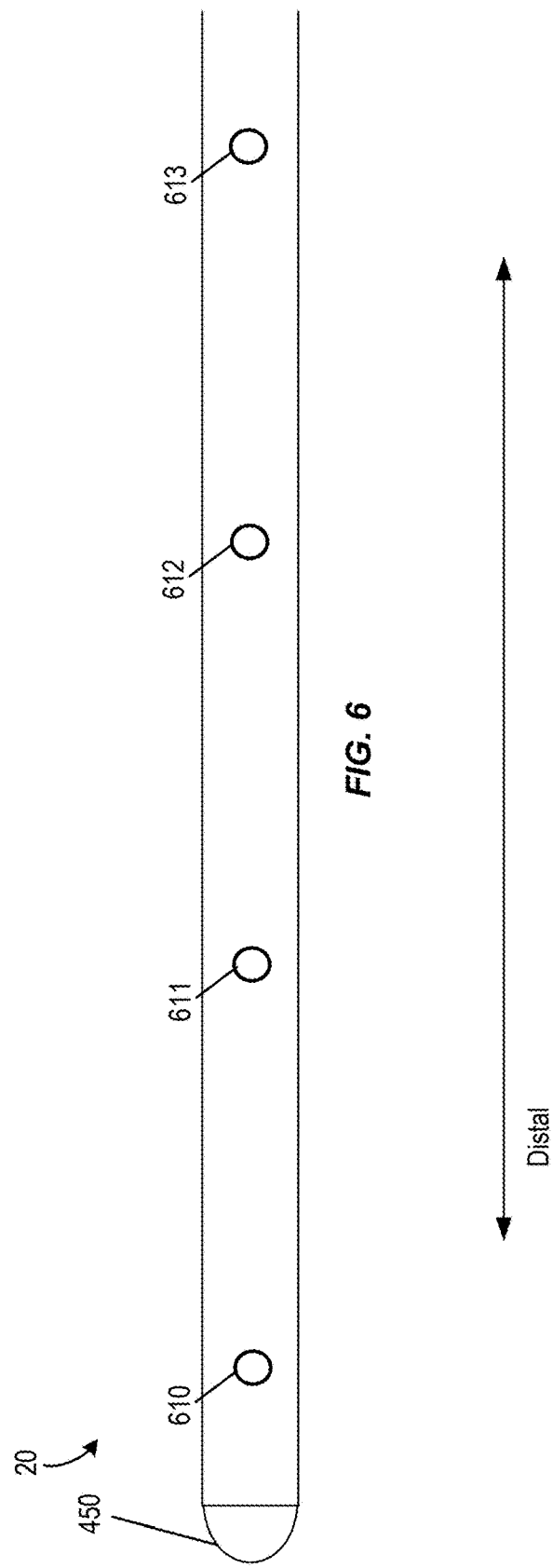
FIG. 6 illustrates a schematic view of the distal portion of the lead with electrodes removed to show apertures for coupling conductors with the electrodes.

FIG. 6 illustrates a schematic view of the distal portion of the lead 20 with electrodes removed to show apertures for coupling conductors with the electrodes. In some embodiments, the neurostimulation lead may include one or more apertures to enable conductors, which may extend within the interior of the lead body, to couple with the electrodes and/or connector interfaces, which may be disposed along the exterior portions of the lead body. In some embodiments, the lead body may have one or more distal apertures along the distal portion. In some embodiments, each of the distal ends of the one or more conductors may exit the interior of the lead body via a respective distal aperture to couple with a respective electrode. For example, referencing FIG. 6, the apertures 610, 611, 612, and 613 which correspond respectively to electrodes 410, 411, 412, and 413 enable conductors to couple with respective electrodes. The term "apertures" as used herein refers to any suitable opening for allowing a conductor to exit the interior of the lead body. Apertures may be round holes (as illustrated in FIG. 6), rectangular holes, slits, or any other suitable openings. In some embodiments, the distal ends of the conductors may physically exit the interior of the lead body and directly couple with the electrodes. In other embodiments, the distal ends of the conductors may indirectly "exit" the interior of the lead body by coupling with the electrodes via one or more intermediary conductive components that exit the interior of the lead body.

In some embodiments, the lead body may have one or more proximal apertures along the proximal portion. In some embodiments, each of the proximal ends of the one or more conductors may exit the interior of the lead body via a respective proximal aperture to couple with a respective connector interface. The proximal apertures may be similar to the distal apertures described above. The conductors may couple with the connector interfaces similar to how they may couple with the electrodes as described above. That is, in some embodiments, the proximal ends of the conductors may physically exit the interior of the lead body and directly couple with the connector interfaces. In other embodiments, the proximal ends of the conductors may indirectly "exit" the interior of the lead body by coupling with the connector interfaces via one or more conductive intermediary components that exit the interior of the lead body.

In some embodiments, as conductors exit the interior of the lead body from the apertures, they may leave behind gaps in the interior of lead body. These gaps may be fluidically coupled to the exit sites through which the conductors exit the interior of the lead body, and as a result, may be susceptible to an ingress of body fluids from the surrounding environment of the implant location. These body fluids include electrolytes, and as such, could serve as a pathway for current to leak by conducting away from the intended target (e.g., nerve tissue external to the lead body) and toward the interior of the lead. This may create an alternative or additional current pathway within the interior of the lead between electrodes. Neurostimulation systems are often implanted for extended periods of time, and this current leakage may increase and compound over time as increasing amounts of body fluid migrate into the lead body.

As a result, periodic recalibrations may be required to effectuate optimal therapy at prescribed stimulation levels. For example, electrical output by an electrode may need to be increased to accommodate for current leakage within the interior of the lead so as to achieve a prescribed stimulation level. The stimulation level may be described, for example, by the amplitude, frequency, or other parameter of the electrical stimulation that indicates an amount or strength of electrical energy delivered by a pulse generator. Frequent recalibration can prove to be an inconvenience for patients. The need for frequent recalibration may also result in noncompliance from some patients, thereby reducing the efficacy of neurostimulation for this patient. Additionally, the recalibrations typically involve increasing the required energy output by a pulse generator (e.g., increasing the amplitude, frequency, etc.) to compensate for leakage, which may reduce battery life of the pulse generator. This may be especially problematic in an implantable pulse generator (IPG) with a nonrechargeable battery (e.g., requiring surgery for replacement of the battery), but it is also an issue with an IPG having a rechargeable battery (e.g., requiring more frequent charging of the battery). Similarly, current leakage also affects external pulse generators (EPGs), which would need to have batteries replaced or recharged more frequently than would be optimal.

FIG. 7 illustrates an example embodiment of the lead 20 with a filler element 440 at the distal end of the lead 20. In some embodiments, the neurostimulation lead may include a distal filler element configured to occupy at least a portion of one or more gaps in the interior of the lead body. The distal filler element may include an electrically nonconductive material, and may be configured to prevent electrical conduction within the lead body. Referencing the example illustrated in FIG. 7, at segment D3, a gap exists due to the conductor 523 exiting the interior of the lead body via the aperture 613 to couple with the electrode 413; at segment D2, a larger gap exists due to the conductor 522 also exiting the interior of the lead body via the aperture 612 to couple with the electrode 412; at segment D1, an even larger gap exists due to the conductor 521 exiting via the aperture 611 to couple with the electrode 411; and at segment DO, an even larger gap exists due to the conductor 520 exiting via the aperture 610 to couple with the electrode 410. In this illustrated example, the filler element 440 is configured to occupy at least a portion of these gaps. As illustrated in FIG. 7, the filler element 440 extends through segments D0, D1, and D2. In this example, there is no filler element in segment D3, because the gap size in segment D3 may be sufficiently small such that ingress of body fluid would be minimal or negligible. However, in another example embodiment, the segment D3 may also include a filler element. By occupying the gaps, the electrically nonconductive filler element may prevent or reduce the ingress of body fluid into the lead body, and may thus prevent or reduce current leakage. The filler element may be disposed within the interior of the lead body in any suitable configuration, and may be disposed in configurations that optimize the amount of space occupying the gaps. For example, referencing FIG. 7, the filler element 440 may be coiled around the lumen so as to best conform to the gaps left by the coiled conductors as they exit the lead body in the illustrated example. In this example, the one or more conductors may be coiled around the lumen at a first pitch, and the first filler element is coiled around the lumen at a second pitch, the second pitch being substantially the same as the first pitch. Alternatively, the second pitch may be different from the first pitch. In another example lead, where conductors are disposed within the lead body in a substantially straight and uncoiled configuration, the filler element may be substantially straight and uncoiled to best conform to gaps left by the conductors.

In some embodiments, the filler element may be further optimized to account for differences in gap size along the length of the lead body. Referencing the example in FIG. 7, as discussed above, the gap sizes of the different segments of the lead 20 vary, with segment D3 having the smallest gap size (e.g., since only one conductor has terminated or exited the interior of the lead body at this segment) and segment D0 having the largest gap size (e.g., since all conductors have terminated or exited the interior of the lead body at the segment). The filler element 440 may be sized to account for this change in gap size. For example, portions of the filler element 440 may be sized to optimally occupy the gaps corresponding to the segments in which they are to be disposed. In this example, the portion of the filler element 440 configured to be disposed in segment D0 may be sized to optimally occupy the gap in segment D0, and the portion of the filler element 440 configured to be disposed in segment D2 may be sized to optimally occupy the gap in segment D2. In this example, the portion of the filler element 440 corresponding to segment D2 may have a larger volume than the portion of the filler element 440 corresponding segment D1. As another example, the filler element 440 may include a multi-filar structure with multiple filars to account for varying gap sizes. In this example, referencing FIG. 7 again, the filler element 440 may be a structure including four separate filars to account for varying gap sizes in the four different segments. In this example, a portion of the filler element 440 corresponding to segment D0 may include four filars (e.g., to account for four missing conductors), a portion of the filler element 440 corresponding to segment D1 may include three filars (e.g., to account for three missing conductors), a portion of the filler element 440 corresponding to segment D2 may include two filars (e.g., to account for two missing conductors), and a portion of the filler element 440 corresponding to segment D3 may include one filar (e.g., to account for one missing conductor).

FIG. 8 illustrates an example embodiment of the lead 20 with a filler element 445 at the proximal end of the lead 20. In some embodiments, a proximal filler element may be included at the proximal portion to occupy at least a portion of the gaps at a proximal portion of the neurostimulation lead. For example, referencing FIG. 8, the filler element 445 is configured to occupy at least a portion of the gaps created as the conductors 520, 521, 522, and 523 exit the interior of the lead body at the proximal portion of the lead 20 (via the apertures 830, 831, 832, and 833, respectively) to couple with the connector interfaces 430, 431, 432, and 433, respectively. As discussed above with respect to the distal portion of the neurostimulation lead, gap sizes may vary across different segments of the proximal portion of the neurostimulation lead as conductors exit or terminate at different aperture points. For example, referencing FIG. 8, the segment P3 has the smallest gap size (resulting from one missing conductor 520), the segment P2 two has a larger gap size (resulting from two missing conductors 520 and 521), the segment P1 has an even larger gap size (resulting from three missing conductors 520, 521, and 522), and the segment P0 has the largest gap size (resulting from for missing conductors 520, 521, 522, and 523).

As discussed above, a filler element may include only a single filar or alternatively may be a multi-filar structure. The filler elements (or filars making up the filler elements) may be of any suitable shape. For example, a filler element may include a flattened ribbon-like filar, which may be rectangular, tapered, triangular, elliptical, or any other suitable shape. As another example, the filler element may include a non-flattened filar, which may have a cross-section that is circular, rectangular, triangular, elliptical, or any other suitable shape. Filler elements (or filars making up the filler elements) may be of any suitable size or volume. In some embodiments, a filler element may include a filar having a length of 10 to 60 mm. In some embodiments, a filler element may include a filar having a diameter of 0.03 to 0.3 mm. In some embodiments, a filler element may include a ribbon-like filar (e.g., a rectangular ribbon similar to the filler element 440 illustrated in FIG. 7) having a width of 0.01 to 2 mm. The dimensions of filler elements may be selected based on the dimension of the conductors, the gap size, number of electrodes, electrode dimensions, electrode pitch, and/or length of the lead.

Filler elements may be composed of one or more electrically nonconductive materials, such that the filler elements are electrically nonconductive. For example, filler elements may be composed at least in part of a polymer material, such as a polyurethane material, a silicone material, high-density polyethylene (HDPE), poly carbonates, or a suitable plastic material. In some embodiments, filler elements may be short segments of inactive conductors (with insulative coatings). Using segments of conductors can help simply manufacturing and supply costs.

In some embodiments, filler elements used in the neurostimulation lead may be composed of substantially the same material as the surrounding lead body. For example, the lead body and a filler element disposed within the lead body may both be composed at least in part of a polymer material, such as a polyurethane material. Having the filler elements be the same material as the surrounding lead body may help with sealing apertures of the lead body during, for example, the reflow process described below.

In some embodiments, a neurostimulation lead may have a filler element only at the distal end of the neurostimulation lead. In other embodiments, a neurostimulation lead may have a filler element only at the proximal end of the neurostimulation lead. In other embodiments, a neurostimulation lead may have a filler element at both the proximal end and the distal end of the neurostimulation lead. In these embodiments, the filler element at the proximal end may be substantially of the same type as the filler element at the distal end, or alternatively may be different. For example, the filler element at one end may be a single filar structure and the filler element at the other end may be a multi-filar structure. As another example, the filler element at one end may be a coiled structure and the filler element at the other end may be an uncoiled structure (e.g., to conform to the configuration of the conductors when the conductors are coiled at one end and uncoiled at the other end).

In some embodiments, the neurostimulation lead may include any number of markers for aiding in locating the lead within a patient, for example during a lead positioning process or during a follow-up monitoring/check-up to ensure proper lead placement. In some embodiments, the neurostimulation lead may include one or more visual markers (e.g., radiopaque markers) that may be visible using an imaging system. For example, referencing FIG. 4, the lead 20 may include a number of markers such as the visual markers 470.

Experimental data supports the effectiveness of the use of filler elements in preventing or reducing current leakage. Three different types of leads were tested, and a summary of the testing data is shown in the tables below. The three different types of leads tested were: a conventional reference lead with no filler element (Table 1), a lead according to the disclosure herein having a coiled rectangular ribbon-shaped polyurethane filler element (Table 2), and a lead according to the disclosure herein having a coiled bi-filar polyurethane filler element (Table 3). Testing was conducted by submerging the leads in a saline solution that mirrored electrolyte concentrations of body fluid that neurostimulation leads would typically be surrounded by when implanted within a patient. Once the leads were submerged, voltage measurements were taken across different pairs of electrode of the lead to measure resistances between the different pairs of electrodes. Each of the leads had four electrodes (E0, E1, E2, and E3) arranged linearly along the lead body. A resistance between the pairs of electrodes that is equal to or greater than 50 kΩ may be an indication that the saline solution has not ingressed within the lead body to cause appreciable current leakage—that is, there is not an appreciable electrical pathway between the electrodes that would decrease the resistance between the electrodes (which is afforded by nonconductive polyurethane in the tested leads). By contrast, a resistance that is less than 50 kΩ may be an indication that there is some current leakage, and the lower the resistance, the greater the current leakage. Referencing Table 1, there is a significant drop in resistance in the reference lead. For example, the resistance between E0 and E1 is 9.53 kΩ, the resistance between E0 and E2 is 20.55 kΩ, the resistance between E0 and E3 is 24.22 kΩ, and the resistance between E1 and E2 is 11.08 kΩ. Referencing Tables 2 and 3 (which show data for leads including coiled polyurethane filler elements), the resistances between all of the tested pairs of electrodes is greater than 50 kΩ, indicating that there is no appreciable current leakage due to ingress of saline solution. In this test, a passing grade was awarded for each pair of electrodes if it had a resistance greater than or equal to 25 kΩ. As reflected in Table 1 below, none of the pairs of electrodes passed in the reference lead with no filler element, in direct contrast to the leads with filler elements (see Tables 2 and 3).

TABLE 1

Reference Lead with No Filler Element

| From (electrode) | To (electrode) | R [kΩ] | Pass? (R ≥ 25 kΩ) |
|---|---|---|---|
| 0 | 1 | 9.53 | NO |
| 0 | 2 | 20.55 | NO |
| 0 | 3 | 24.22 | NO |
| 1 | 2 | 11.08 | NO |
| 1 | 3 | 14.87 | NO |
| 2 | 3 | 8.37 | NO |

TABLE 2

Lead with Rectangular Ribbon Coil

| From (electrode) | To (electrode) | R [kΩ] | Pass? (R ≥ 25 kΩ) |
|---|---|---|---|
| 0 | 1 | 1000.00 | YES |
| 0 | 2 | 1000.00 | YES |
| 0 | 3 | 1000.00 | YES |
| 1 | 2 | 1000.00 | YES |
| 1 | 3 | 1000.00 | YES |
| 2 | 3 | 1000.00 | YES |

TABLE 3

Lead with Bifilar Coil

| From (electrode) | To (electrode) | R [kΩ] | Pass? (R ≥ 25 kΩ) |
|---|---|---|---|
| 0 | 1 | 1000.00 | YES |
| 0 | 2 | 1000.00 | YES |
| 0 | 3 | 1000.00 | YES |
| 1 | 2 | 1000.00 | YES |
| 1 | 3 | 1000.00 | YES |
| 2 | 3 | 1000.00 | YES |

IPGs and EPGs apply electrical energy for a neurostimulation from a power source (e.g., a battery) having a finite power supply. In many cases (e.g., in sacral neuromodulation use cases), IPGs once implanted are typically expected to have a lifespan of 5 to 15 years. As mentioned previously, current leakage over time causes the need to recalibrate periodically to adjust power output upward to account for the current leakage to maintain effectiveness of therapy. This takes a toll on battery life, and is particularly problematic for IPGs with nonrechargeable batteries, which would need to be surgically explanted for battery replacement. It is also problematic for IPGs that have rechargeable batteries, because it would require more frequent charging of the battery. This is not only an inconvenience for the patient, but the increased number of charging cycles may reduce the lifespan of the battery. Similarly, current leakage also affects external pulse generators EPGs, which would need to have batteries replaced or recharged more frequently than would be optimal.

FIG. 9 illustrates an example method 900 of manufacturing a neurostimulation lead. Any suitable method may be used in manufacturing the neurostimulation leads described herein. Referencing FIG. 9, in some embodiments, the method of manufacture may include, at step 910, providing a flexible tubular member from a first electrically nonconductive material, wherein the tubular member comprises a distal portion and a proximal portion. This tubular member may be a hollow structure that forms the scaffolding for what will become the lead body when manufacturing is completed. The tubular member may include one or more distal apertures at the distal portion of the tubular member and may further include one or more proximal apertures at the proximal portion of the tubular member. In some embodiments, the manufacturing method may include forming the apertures via any suitable means. For example, the apertures may be formed by using a laser cutting method, by using a sharpened element, by molding the tubular member to include the apertures, etc. Referencing FIG. 6 for example, the apertures may be circular holes (e.g., the apertures 610, 611, 612, 613), rectangular openings, slits, etc. The tubular member may be composed of any suitable material, and may be electrically nonconductive. For example, the tubular member may be composed of a polymer material, such as a polyurethane material.

At step 920, the method may include disposing one or more conductors around an elongate mandrel in a coiled manner. A mandrel may be any elongate structure suitable for acting as a support for ultimately positioning conductors and filler elements within the tubular member. The conductors may be elongate, drawn-out wires. The conductors may be made of any conductive material (e.g., a metal that is suitably ductile and malleable to allow for drawing out the wires and adequate shaping). Each of the conductors may be surrounded by an insulative material or coating. In some embodiments, the conductors may be pre-coiled and slid onto the elongate mandrel. In other embodiments, the conductors may be substantially straight conductors that are coiled by winding the conductors around the elongate mandrel. In yet other embodiments, the method may not require coiled conductors, in which case the conductors may be maintained in an uncoiled, substantially straight manner.

At step 930, the method may include placing the elongate mandrel within an interior of the tubular member. At step 940, the method may include mounting one or more electrodes along an exterior of the distal portion of the tubular member, the electrodes comprising a first electrically conductive material. At step 950, the method may include mounting one or more connector interfaces along an exterior of the proximal portion of the tubular member, the connector interfaces comprising a second electrically conductive material. The electrodes and connector interfaces may be mounted by any suitable means. For example, they may be mounted using an adhesive, a bolt or screw mechanism, or simply a friction fit.

At step 960, the method may include for each conductor, causing a distal end of the conductor to exit the distal portion of the tubular member via a respective distal aperture to couple with a respective electrode. This step may also include causing a proximal end of the conductor to exit the proximal portion of the tubular member via a respective proximal aperture to couple with a respective connector interface. In some embodiments, the distal ends of the conductors may be coupled directly to one or more respective electrodes (e.g., by way of welding) or coupled indirectly to one or more respective electrodes (e.g., via one or more components). For example, referencing FIG. 7, the conductor 523 may be welded to the electrode 413, the conductor 522 may be welded to the electrode 412, the conductor 521 may be welded to the electrode 411, and the conductor 510 may be welded to the electrode 410. The conductors may be coupled to the connector interfaces in a similar manner.

At step 970, the method may include inserting a first filler element into the interior of the tubular member to occupy at least a portion of one or more gaps in the interior of the tubular member resulting from the exit of one or more of the one or more conductors from the tubular member, wherein the first filler element comprises a second electrically nonconductive material. In some embodiments, the first filler element may be inserted at the distal portion of the tubular member, and a second filler element may be inserted at the proximal portion of the tubular member. In some embodiments, the filler elements may be caused to be coiled, particularly when the conductors are coiled. In these embodiments, the conductors may be coiled at a first pitch, and the filler elements may be coiled at a second pitch. The first pitch may substantially be the same as the second pitch, or may alternatively be different from the second pitch. In embodiments where the filler elements are coiled, the filler elements may be pre-coiled and slid onto the elongate mandrel. In other embodiments, the conductors may be substantially straight conductors that are coiled by winding the conductors around the elongate mandrel. The filler elements may be inserted into the tubular member after the elongate mandrel has already been inserted (and then slid or coiled around the elongate mandrel). Alternatively, the filler elements may be slid or coiled around the elongate mandrel prior to insertion of the elongate mandrel. For example, the conductors and filler elements may be positioned on or around the elongate mandrel prior to placing the elongate mandrel within the interior of the tubular member.

In the case of a filler element that is a multi-filar structure, the fillers of the multi-filar structure may be compiled together (e.g., bonded to each other) prior to placing the multi-filar structure within the lead body. Alternatively, each of the filars may be inserted into the lead body separately. For example, referencing FIG. 7, a first filar may be inserted to extend from the distal tip 450 to the aperture 613; a second filar having a smaller length may be inserted to extend from the distal tip 450 to the aperture 612; a third filar having an even smaller length may be inserted to extend from the distal tip 450 the aperture 611; and a fourth filar having an even smaller length may be inserted to extend from the distal tip 450 to the aperture 610. The resulting filler element has varying thickness among the different segments D0, D1, D2, and D3.

In some embodiments, when the lead includes two or more electrodes, the method may include placing one or more spacers in between the electrodes and connector interfaces. The spacers may be any suitable structural element that is capable of being placed (e.g., on or around the exterior of the lead body) so as to appropriately space out the electrodes at desired locations along the lead body. The spacers may be made of any suitable material that makes the spacers electrically nonconductive. For example, the spacers may be made of a polymer material such as a polyurethane material. In some embodiments, the spacers may be made of substantially the same material as the tubular member (e.g., a polymer material such as polyurethane). In some embodiments, the spacers, the filler element, and the tubular member may all be made of substantially the same material (e.g., a polymer material such as polyurethane). The spacers may be placed prior to mounting the electrodes and connector interfaces or may alternatively be placed after mounting the electrodes and connector interfaces.

At step 980, the method may include causing at least the first electrically nonconductive material to reflow and set so as to secure at least a portion of the one or more conductors and the first filler element within the tubular member. The reflow process may involve heating the assembled components of the lead to a suitable temperature so as to melt materials of particular elements of the lead, such as the tubular member and/or the filler element (and not other elements such as the conductors, the electrodes, the connector interfaces, etc.). When the melted materials cool down and set, a seal is formed that may secure various elements of the lead, such as the conductors, the filler elements, etc., within the lead body. This reflow step may also cause the melted material to flow around the conductors at the exit points to fill in any gaps in the apertures. In some embodiments, when spacers are used as described above, the reflow step also causes the material of the spacer to reflow and set so as to further aid with sealing the apertures along the lead body.

At step 990, the method may include removing the elongate mandrel, which may leave behind a lumen, which may be configured to receive a stylet to aid with the implantation procedure, as described above.

Particular embodiments may repeat one or more steps of the method of FIG. 9, where appropriate. Although this disclosure describes and illustrates particular steps of the method of FIG. 9 as occurring in a particular order, this disclosure contemplates any suitable steps of the method of FIG. 9 occurring in any suitable order. For example, the electrodes and connector interfaces may be mounted to the tubular member prior to placing the elongate mandrel within the tubular member. As another example, the filler element may be inserted prior to placing the elongate mandrel within the tubular member. Moreover, although this disclosure describes and illustrates an example method for manufacturing a neurostimulation lead, including the particular steps of the method of FIG. 9, this disclosure contemplates any suitable method for manufacturing a neurostimulation lead, including any suitable steps, which may include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

What is claimed is:

1. An implantable neurostimulation lead comprising:
a lead body having a proximal portion and a distal portion, wherein the lead body has one or more proximal apertures along the proximal portion and one or more distal apertures along the distal portion;
a lumen extending the length of the lead body;
one or more electrodes positioned along an exterior of the lead body at the distal portion of the lead body;
one or more connector interfaces positioned along the exterior of the lead body at the proximal portion of the lead body, each connector interface configured to engage with a respective connector of a pulse generator;
one or more conductors extending through an interior of the lead body, each of the conductors having a proximal end and a distal end, wherein the proximal end exits the interior of the lead body via a respective proximal aperture to couple with a respective connector interface, and wherein the distal end exits the interior of the lead body via a respective distal aperture to couple with a respective electrode, each conductor coupling a respective electrode with a respective connector interface; and
a multi-filar filler element comprising a plurality of coiled filars positioned to occupy at least a portion of one or more gaps in the interior of the lead body resulting from the exit of one or more of the one or more conductors from the lead body, wherein the first filler element comprises an electrically nonconductive material, wherein the number of filars decreases in the proximal direction at the distal portion of the lead body.

2. The implantable neurostimulation lead of claim 1, wherein the one or more conductors are coiled around the lumen, and wherein the first multi-filar filler element is coiled around the lumen.

3. The implantable neurostimulation lead of claim 2, wherein the one or more conductors are coiled around the lumen at a first pitch, and wherein the first multi-filar filler element is coiled around the lumen at a second pitch, the second pitch substantially the same as the first pitch.

4. The implantable neurostimulation lead of claim 2, wherein the one or more conductors are coiled around the lumen at a first pitch, and wherein the first multi-filar filler element is coiled around the lumen at a second pitch, the second pitch being different from the first pitch.

5. The implantable neurostimulation lead of claim 1, wherein the one or more electrodes comprises four electrodes and the one or more connector interfaces comprises four connector interfaces, and wherein the multi-filar filler element comprises up to three filars.

6. The implantable neurostimulation lead of claim 1, wherein:
the one or more electrodes comprises a first electrode and a second electrode; and
the one or more conductors comprises a first conductor and a second conductor, wherein a distal end of the first conductor exits the interior of the lead body via a first distal aperture and a distal end of the second conductor exits the interior of the lead body via a second distal aperture, the first distal aperture being distal to the second distal aperture;
wherein the multi-filar filler element is sized to extend between the first distal aperture and the second distal aperture along the interior of the lead body, and wherein the multi-filar filler element is sized to extend between the second distal aperture and a subsequent distal aperture along the interior of the lead body.

7. The implantable neurostimulation lead of claim 1, wherein:
the one or more connector interfaces comprises a first connector interface and a second connector interface; and
the one or more conductors comprises a first conductor and a second conductor, wherein a proximal end of the first conductor exits the interior of the lead body via a first proximal aperture and a proximal end of the second conductor exits the interior of the lead body via a second proximal aperture, the second proximal aperture being distal to the first proximal aperture;
wherein the multi-filar filler element is sized to extend between the first proximal aperture and the second proximal aperture along the interior of the lead body and wherein the multi-filar filler element is sized to extend between the second proximal aperture and a subsequent proximal aperture along the interior of the lead body.

8. The implantable neurostimulation lead of claim 1, further comprising a second filler element is disposed at the proximal portion of the lead, the second filler element comprising an electrically nonconductive material.

9. The implantable neurostimulation lead of claim 1, wherein the first multi-filar filler element comprises a polyurethane material.

10. The implantable neurostimulation lead of claim 9, wherein the lead body comprises a polyurethane material.

11. The implantable neurostimulation lead of claim 1, wherein the first multi-filar filler element comprises a solid extrusion.

12. The implantable neurostimulation lead of claim 1, wherein the first multi-filar filler element comprises an adhesive or cured thermoplastic or thermoset polymer material that is configured to be injected into the at least one or more gaps in the interior of the lead body.

13. The implantable neurostimulation lead of claim 1, wherein the first multi-filar filler element has a length of 10 to 60 mm.

14. The implantable neurostimulation lead of claim 1, wherein the first multi-filar filler element has a diameter of 0.03 to 0.3 mm.

15. The implantable neurostimulation lead of claim 1, wherein the first multi-filar filler element comprises a ribbon-like filar structure having a width of 0.01 to 2 mm.

16. An implantable neurostimulation lead comprising:
a lead body having a proximal portion and a distal portion;
a plurality of electrodes positioned in series along an exterior of the lead body at the distal portion of the lead body;
a plurality of conductors extending through an interior of the lead body, each of the conductors having a proximal end and a distal end, wherein the distal end of each conductor terminates due to each of the electrodes coupling with one of the plurality of electrodes; and
a multi-filar filler element comprising plurality of coiled filars positioned to occupy a distal gap in the interior of the distal portion of the lead body created by the termination of the plurality of conductors, and wherein the volume to be filled by the filler element in the distal portion of the lead body increases along the length of the lead in a distal direction due to the increasing size of the distal gap resulting from the sequential termination of the electrodes, and wherein the number of filars decreases in the proximal direction at the distal portion of the lead body.

17. The implantable neurostimulation lead of claim 16, wherein each of the plurality of conductors are coiled around a lumen, and wherein the filler element is coiled around the lumen.

18. The implantable neurostimulation lead of claim 17, wherein each of the plurality of conductors are coiled around the lumen at a first pitch, and wherein the filler element is coiled around the lumen at a second pitch, and wherein the second pitch is different from the first pitch.

19. The implantable neurostimulation lead of claim 16, wherein the filler element is injected into the distal portion of the lead body.

20. An implantable neurostimulation lead comprising:
a lead body having a proximal portion and a distal portion;
a plurality of electrodes positioned along an exterior of the lead body at the distal portion of the lead body;
a plurality of connector interfaces positioned in series along the exterior of the lead body at the proximal portion of the lead body, each connector interface configured to engage with a respective connector of a pulse generator;
a plurality of conductors extending through an interior of the lead body, each of the conductors having a proximal end and a distal end, wherein the proximal end of each conductor is coupled with one of the plurality of connector interfaces; and
a multi-filar filler element comprising a plurality of coiled filars positioned to occupy a proximal gap in the interior of the distal portion of the lead body created by the coupling of the proximal end of each of the plurality of conductors with one of the plurality of connector interfaces, and wherein the volume to be filled by the filler element in the proximal portion of the lead body decreases along the length of the lead in a distal direction due to the decreasing size of the proximal gap resulting from the sequential coupling of the electrodes with the connector interface, and wherein the number of filars decrease in the distal direction at the proximal portion of the lead body.

21. The implantable neurostimulation lead of claim 20, wherein each of the plurality of conductors are coiled around a lumen, and wherein the filler element is coiled around the lumen.

22. The implantable neurostimulation lead of claim 21, wherein each of the plurality of conductors are coiled around the lumen at a first pitch, and wherein the filler element is coiled around the lumen at a second pitch, and wherein the second pitch is different from the first pitch.

23. The implantable neurostimulation lead of claim 20, wherein the filler element is injected into the proximal portion of the lead body.

* * * * *